March 31, 1953 E. PRUSHEK Plant Pat. 1,177
CHRYSANTHEMUM PLANT
Filed Dec. 17, 1951
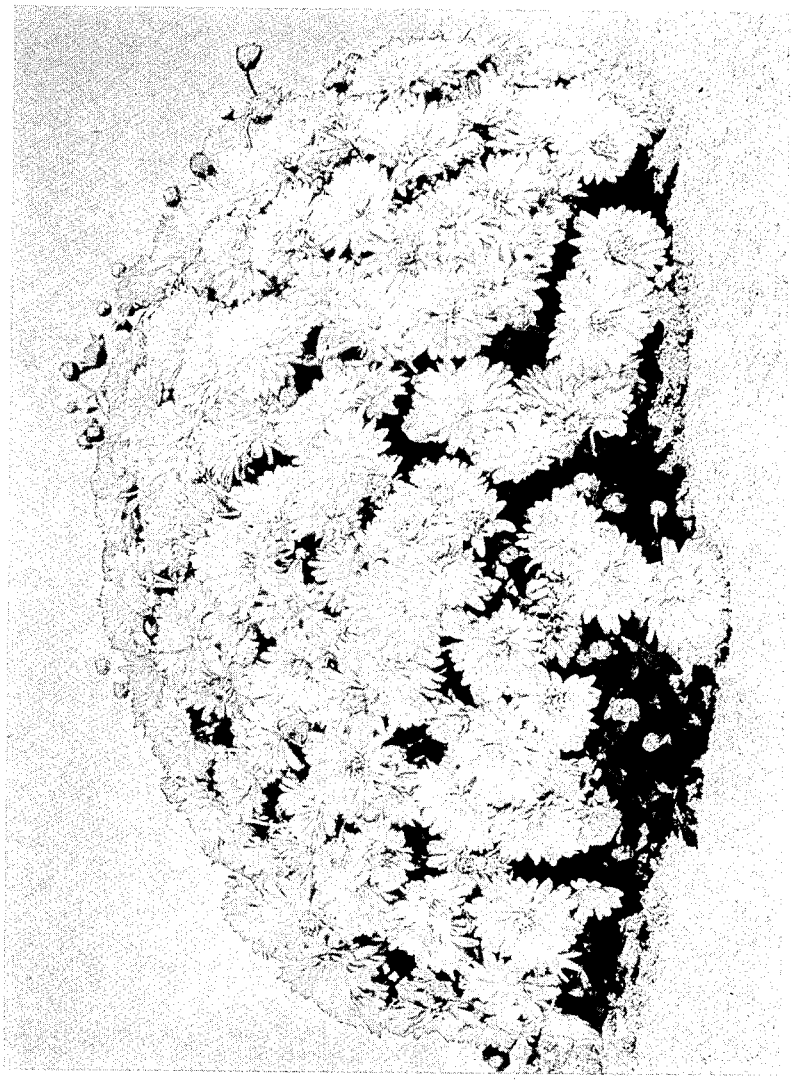
INVENTOR:
Emil Prushek
By. Robb & Robb,
Attorneys Patented Mar. 31, 1953

Plant Pat. 1,177

UNITED STATES PATENT OFFICE 1,177

CHRYSANTHEMUM PLANT

Emil Prushek, Niles, Mich., assignor to The R. M. Kellogg Company, Three Rivers, Mich., a corporation of Michigan Application December 17, 1951, Serial No. 262,128

1 Claim. (Cl. 47—60)

My present invention comprises a new and distinct variety of chrysanthemum plant, the result of crossing the variety "Summer Sunset" Plant Patent No. 561 and the unpatented variety "Santa Claus."

The object of my invention was to produce a new variety of chrysanthemum of the cushion type having blossoms of a true chrysanthemum crimson color (Horticultural Colour Chart of the British Colour Council).

The development of the present new variety has resulted from a program which I have been conducting of careful selection and cross-breeding with the view of producing new varieties of chrysanthemum of the cushion type and having more dwarf and compact habits of growth, and having different desired colors in reference to the blooms of such plants.

The result of the specific hybridization above mentioned has been to produce my present new and distinct variety of chrysanthemum plant, characterized by the crimson color of its blooms, the very double arrangement of its petals, its dwarf, compact, and floriferous habits of growth, its long and continuous blooming season, and its habit of producing numerous and successive blooms with fresh flowers rising above and covering the earlier fading ones.

More specifically, the blooms of my new variety are of a true chrysanthemum crimson color (Horticultural Colour Chart of the British Colour Council). As grown in the vicinity of Niles, Michigan, under uniform culture, first year plants of my new variety grown from soft top cutting have an average height of fourteen inches and an average diameter of twenty inches.

While my new variety bears a closer resemblance to its parent "Santa Claus" than it does to its other parent "Summer Sunset," my new variety differs from both of its parents and from other known varieties in many respects.

In comparing the color of the bloom of my new variety with the color of the blooms of the variety "Santa Claus" it is to be noted that the color of the blooms of the latter is cardinal red whereas the color of the blooms of my new variety is a true chrysanthemum crimson. The petal arrangement in the variety "Santa Claus" is not fully double and the blooms show many stamens when fully opened. On the other hand the petal arrangement in my new variety is completely double, making it difficult to find any stamens for further breeding; in fact, stamens in my new variety are rare and small.

Under the conditions of culture above mentioned, in the region of Niles, Michigan, first year plants of my new variety produce rather soft, high pompon blooms averaging two inches in diameter. Under the same conditions of culture, in the region of Niles, Michigan, "Santa Claus" variety produces semi-double blooms on a plant twenty-six inches in diameter and eighteen inches high, on the average. Thus plants of my new variety average about half the volume of plants of the "Santa Claus" variety, but my new variety is more compact and floriferous and carries more blooms than the larger, more open plants of the "Santa Claus" variety.

When grown in the region of Niles, Michigan, blooms of the "Santa Claus" variety open about October 5, about ten days later than the blooms of my new variety. The "Santa Claus" variety blooms more sparingly, the flowers not covering the plant. My new variety is dwarfer and more compact than "Santa Claus" and my new variety has total coverage of crimson colored blooms producing a general effect of a red blaze.

The flowers of the "Santa Claus" variety open later for a shorter season before frost than is the case with the blooms of my new variety, and the blooms of "Santa Claus" do not cover the bush completely and do not provide complete coverage for the earlier fading flowers. On the other hand, my new variety blooms earlier than "Santa Claus" and the numerous and successive blooms of my new variety provide a long blooming season with fresh flowers rising above and covering the earlier fading ones.

My new variety has been found to retain its distinctive characteristics through successive asexual reproduction.

The accompanying drawing forming a part hereof shows a typical plant of my new variety of chrysanthemum.

The following is a detailed description of my new variety of chrysanthemum plant, the color references being to the Horticultural Colour Chart of the British Colour Council:

Classification: Botanic — *Chrysanthemum hortorum.*

*Flower*

*Blooming habit*: Blooms profusely and continuously midseason in fall beginning about September 25th, producing a succession of blooms for a long season and to cover earlier fading flowers.

Bud:

*Size.*—Small.

*Form.*—Globular. Is not affected by wet weather or hot weather.

*Color.*—When sepals first divide—Oxblood red, 00823. When petals begin to unfurl—Oxblood red, 00823. When half blown—inside of petal: Chrysanthemum Crimson 824; reverse of petal: Chrysanthemum Crimson 824 lightened by Sulphur Yellow.

*Sepals.*—Smooth edge; stand up.

*Peduncle.*—Medium length; aspect—rough; color — medium green; strength — stiff, erect, slender.

Bloom:

*Size.*—Small. Average size when fully expanded, 2″.

*Borne.*—Singly.

*Stems.*—Medium length, normal strength.

*Form.*—When first open—high center. Permanence—retains its form to the end.

*Petalage.*—Very double, stamens rare. Number of petals under normal conditions about 150.

Color:

*Center of flower.*—Chrysanthemum Crimson 824 lightened by Sulphur Yellow.

*Outer petals.*—Chrysanthemum Crimson 824.

*Base of petals.*—Sulphur Yellow ⅓.

*Inside of petals.*—Chrysanthemum Crimson 824.

*Reverse of petals.*—Chrysanthemum Crimson 824 lightened by Sulphur Yellow.

*General tonality from a distance.*—Brilliant mass of crimson.

*Discoloration.*—General tonality at end of: First week—blazing mass of crimson; third week—a fading to Erythrite Red 0027/1.

Petals:

*Texture.*—Thin, soft. Not affected by hot or wet weather except some fading in unseasonable heat.

*Appearance.*—Velvety inside, shiny outside.

*Form.*—Long, oval, pointed.

*Persistence.*—Hang on and dry.

*Fragrance.*—Characteristic chrysanthemum.

*Lastingness.*—Long.

Genital organs:

*Stamens, Anthers.*—Small, rare.

*Color.*—Yellow.

*Arrangement.*—Regular.

*Stamens, filaments.*—Short. Color—lemon yellow.

*Stigmas.*—Yellow.

*Plant*

Form: Bush.

Growth: Vigorous, branching, compact.

Foliage:

*Size.*—Small.

*Quantity.*—Normal.

*Color (new foliage).*—Upper side—normal green; under side—light green.

*Color* (old foliage).—Upper side—normal; under side—light green.

*Shape.*—Oval pointed.

*Texture.*—Velvety on upper side; rough on under side.

*Edge.*—Serrated.

*Serration.*—Double, deep.

*Leaf stem.*—Color—green; under side—rough.

*Stipules.*—Short, rough.

Wood:

*New wood.*—Color—light green; bark—rough.

*Old Wood.*—Color—green; bark—rough.

I claim:

A new and distinct variety of chrysanthemum plant substantially as herein disclosed, characterized as to novelty by the crimson color of its blooms, the fully double arrangement of its petals, the dwarfer, more compact, and floriferous habit of growth, its earlier and longer blooming period and its characteristic of continuous production of successive blooms with fresh flowers rising above and covering the earlier fading ones.

EMIL PRUSHEK.

No references cited.